United States Patent [19]
Pruitt, Jr.

[11] Patent Number: 5,938,681
[45] Date of Patent: *Aug. 17, 1999

[54] CARDIAC MANIPULATOR FOR MINIMALLY INVASIVE SURGICAL PROCEDURES

[75] Inventor: J. Crayton Pruitt, Jr., Clearwater, Fla.

[73] Assignee: CryoLife Acquisition Corporation, Clearwater, Fla.

[ * ] Notice: This patent issued on a continued prosecution application filed under 37 CFR 1.53(d), and is subject to the twenty year patent term provisions of 35 U.S.C. 154(a)(2).

[21] Appl. No.: 08/843,329

[22] Filed: Apr. 15, 1997

[51] Int. Cl.$^6$ .................................................. A61M 29/00
[52] U.S. Cl. .......................... 606/192; 600/207; 600/208
[58] Field of Search ................................. 600/207, 208, 600/37; 606/192; 604/96

[56] References Cited

U.S. PATENT DOCUMENTS

| | | | |
|---|---|---|---|
| 4,738,666 | 4/1988 | Fuqua | 604/96 |
| 5,496,345 | 3/1996 | Kieturakis et al. | 600/207 |
| 5,514,153 | 5/1996 | Bonutti | 606/192 |
| 5,520,609 | 5/1996 | Moll et al. | 600/207 |

*Primary Examiner*—Michael Buiz
*Assistant Examiner*—Kevin Truong
*Attorney, Agent, or Firm*—Willam A. Birdwell & Associates

[57] ABSTRACT

A cardiac manipulator for minimally invasive surgical procedures. A flexible sac houses one or more inflatable chambers therein, the flexible sac permitting insertion through an access aperture into a patient when the inflatable chambers are deflated. The inflatable chambers each have a fluid conduit connected to an associated valve for introducing a fluid thereinto and removing the fluid therefrom. The flexible sac may be manipulated into a low profile configuration for insertion into and through the access aperture.

14 Claims, 1 Drawing Sheet

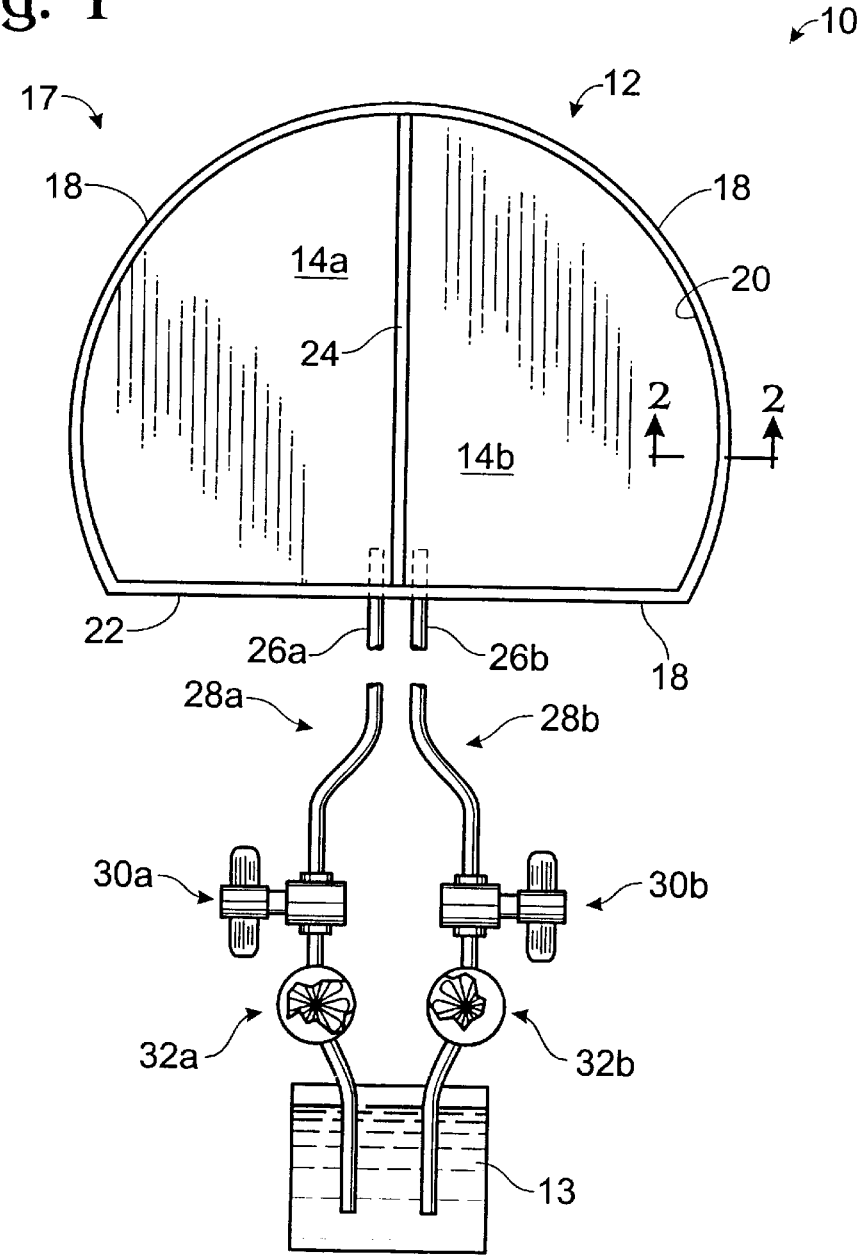
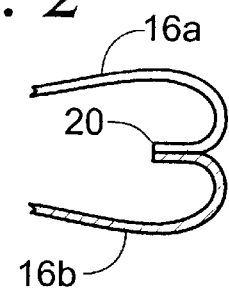
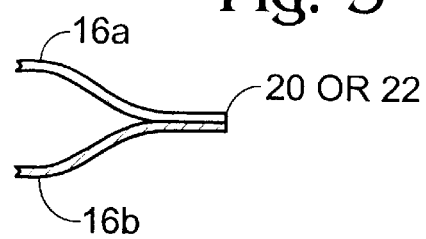

CARDIAC MANIPULATOR FOR MINIMALLY INVASIVE SURGICAL PROCEDURES

BACKGROUND OF THE INVENTION

This invention relates to devices employed in cardiac bypass surgery, particularly to such devices employed for minimally invasive procedures.

Typical coronary bypass surgery is a major and traumatic procedure from which recovery is difficult and protracted. A very large incision is required and the patient's chest must be "cracked" at the breastbone so that it may be opened wide for the surgeon to gain access to the heart with hands and operating instruments.

Therefore, a minimally invasive procedure for bypass surgery is highly preferable. In such a procedure, a relatively small incision is made over the fourth coastal cartilage or, alternatively, in the upper abdominal midline, the incision being just large enough for a localized operation on the heart or arterial system. Importantly, the patient's ribs do not have to be cut and reattached, though a small portion of cartilage is typically removed. Moreover, the incision, being small, is more easily and quickly healed. It has been found that, often, patients may leave the hospital after such a procedure within one or two days.

However, access to the heart is made more difficult in the minimally invasive procedure. The access aperture is smaller, requiring that the surgical instruments employed must be capable of functioning in very tight quarters. Moreover, minimizing the size of the access aperture to minimize trauma has necessarily required sacrificing the facility with which it is possible to reach and operate on distant locations on the heart and the local arterial system from the aperture.

In the typical coronary bypass procedure, the surgeon often desires to elevate and tilt the heart for improved access for dissecting the graft site as well as for suturing. This has been done by placing laparotomy pads, or rolled towels, underneath the heart. In the minimally invasive procedure, the need is even greater to manipulate the heart to improve access. However, because of the small incision, which is typically about 4 centimeters long, there is not room for placing towels or laparotomy pads underneath the heart.

Accordingly, there is a need for a cardiac manipulator for use in minimally invasive surgical procedures that provides for increasing the surgeon's access to the heart and the local arterial system through a minimally sized access aperture.

SUMMARY OF THE INVENTION

The cardiac manipulator for minimally invasive surgical procedures of the present invention solves the aforementioned problems and meets the aforementioned needs by employing a flexible sac housing one or more inflatable chambers therein, the flexible sac permitting insertion through an access aperture into a patient when the inflatable chambers are deflated. The inflatable chambers each have a fluid conduit connected to an associated valve for introducing a fluid thereinto and removing the fluid therefrom. The flexible sac may be manipulated into a low profile configuration for insertion into and through the access aperture whereafter it may be manipulated and inflated into an open configuration.

Therefore, it is a principal object of the present invention to provide a novel cardiac manipulator for minimally invasive surgical procedures.

It is another object of the present invention to provide such a cardiac manipulator which provides for increased access to distant locations on the heart and the local arterial system.

It is a further object of the present invention to provide such a cardiac manipulator which provides for deployment through a small access aperture.

The foregoing and other objects, features and advantages of the present invention will be more readily understood upon consideration of the following detailed description of the invention, taken in conjunction with the following drawings.

BRIEF DESCRIPTION OF THE DRAWINGS

FIG. 1 is a plan view of a preferred embodiment of a cardiac manipulator for minimally invasive surgical procedures according to the present invention.

FIG. 2 is a section of the cardiac manipulator of FIG. 1, taken along a line 2—2 thereof.

FIG. 3 is a section of a cardiac manipulator according to the present invention having a flat seal seam which is not everted, the section corresponding to the section of FIG. 2.

DETAILED DESCRIPTION OF A PREFERRED EMBODIMENT

Referring to FIGS. 1 and 2, a preferred embodiment of a cardiac manipulator 10 for minimally invasive surgical procedures is shown. The minimally invasive procedure typically employs a very small incision, such as about 4 cm in length, for access to the heart and the proximate arterial system. A cardiac manipulator according to the present invention may be used in a standard procedure but the manipulator 10 is particularly adapted for such a minimally invasive procedure. The manipulator 10 comprises a flexible sac 12 which, preferably, is partitioned, along a partition 24, to form two integral inflatable chambers 14a, 14b.

The sac 12 is preferably made of two plastic or other impermeable, flexible sheets 16a, 16b bonded at a periphery 18. Materials which may be employed for the sac 12 include, but are not limited to polyvinylchloride (PVC), thermoplastic elastomer (TPE), polyethylene, polypropylene, heat seal coated polyester, silicone and polyurethane. It is preferable to minimize any outward protrusion of edges along the sac 12. Accordingly, the sheets are preferably heat sealed together along about a three-quarter or greater portion of the periphery 18, and the resulting form is preferably everted so that an edge 20 is retained inside the sac 12 and is, therefore, inwardly protruding. The resulting form, however, need not be everted to conform to the principles of the invention (see, e.g., FIG. 3). Particularly, the edge 20 may be left to be externally exposed where, because of minimized thickness or the suppleness of the materials for example, it is not sharp enough to cause trauma. Particularly where there is no everting of the sac 12, a greater portion of the periphery 18, or substantially the whole thereof, may be heat sealed together.

Then, and after the insertion of fluid conducting conduits as will be described below, the remaining portion of the periphery 18 is heat sealed to form a substantially fluid-tight sac 12. The remaining portion of the periphery of the preferred embodiment generally having an outwardly protruding edge 22, the sac 12 may otherwise be formed wholly, without bonding discrete materials such as the sheets 16a, 16b together so that it has no edge 20 or 22. The aforedescribed, preferred structure may have decreased costs depending on, inter alia, production quantities.

The partition 24 is also preferably formed by heat sealing, and may divide the sac 12 into substantially equal size chambers 14a, 14b, or may divide the sac into chambers having an unequal size. Further, the shape of the chambers 14a, 14b may be substantially the same or may differ as desired. Further still, there may be any number of chambers 14, including a single chamber 14a. The sac 12 is generally sized according to the size of the heart for which it is intended that the apparatus 10 be used. However, it is not believed that a strict size correspondence of the sac with the size of the organ is required or even always desirable. Moreover, though a substantially round sac 12 is shown herein, the sac is also shaped according to need and may be any desired shape, such as rectangular or oval.

It is to be understood that the sac 12 may employ other flexible materials, such as rubber, and may be sealed in other ways known in the art, such as by adhesive, without departing from the principles of the invention. And while it is advantageous to form the inflatable chambers 14a, 14b out of the sac 12, the invention also contemplates a sac 12 that need not be substantially fluid-tight and which merely contains separate inflatable chambers 14a, 14b.

The inflatable chambers are each in fluid communication with an associated fluid conducting conduit 26a, 26b, for introducing a fluid therein and removing the fluid therefrom, to control the inflation thereof. The conduits 26a, 26b are preferably made of the same or a similar or compatible material as the sheets 16a, 16b and are inserted therebetween before the aforedescribed sealing thereof. The conduits may be advantageously extruded and may be formed of materials which include, but are not limited to PVC, TPEs, silicone, polyethylene, polypropylene and polyurethane. The sheets may be fully or partially sealed around the conduits during the same process. It has been found preferable, however, to employ an adhesive at the junction of the conduits and the sheets as well, to mechanically strengthen the junction in addition to helping further to seal it.

Each conduit 26a, 26b includes, at associated distal ends 28a, 28b thereof, a fluid valve 30a, 30b, for controlling the rate of fluid entry and removal into the chambers 14a, 14b.

OPERATION

The sac 12 may be introduced through the access aperture in the patient in a number of ways. Since it is flexible, it may be folded, e.g., in umbrella or napkin fashion, or it may be wrapped, rolled or twisted into a low-profile configuration for insertion therethrough, whereafter it is caused to assume an open configuration by any desired combination of manipulation and inflation. The sac is preferably positioned with the fingers or with a surgical instrument such as forceps or graspers to a desired location proximate the heart, typically underneath the heart or disposed laterally with respect thereto, or in a combination of these positions. Moreover, the sac 12 may be repositioned as desired. However, an outstanding advantage of the manipulator 10 is that, particularly when including multiple chambers, the manipulator provides for a plurality of elevations, lateral positions and angular inclinations of the heart by adjustment of the degree of inflation of the chambers, as discussed immediately below. Therefore, the manipulator 10 minimizes the need for such repositioning.

Once the manipulator is in place, selective inflation and deflation of the chambers 14a, 14b pushes on or permits relaxation of the associated proximate portion of the heart or arterial system and thereby permits manipulation of the position of one or more areas of interest therein with respect to the access aperture. For example, the sac 12 may be placed underneath the heart so that a portion of the heart lying above the chamber 14a may be moved upwardly by inflating the chamber 14a, and may be moved back downwardly by deflating the chamber 14a. The heart may be tilted, or moved entirely upwardly and downwardly by selected inflation and deflation of the chambers 14a, 14b. As another example, the sac 12 may be placed laterally against the heart, so that the heart may be moved laterally in its entirety or in portions, or it may be twisted by selected inflation and deflation of the chambers. A third example demonstrates the utility of an embodiment which includes two chambers 14a, 14b. The sac 12 is manipulated so that one of the chambers is positioned laterally against the heart, while the other chamber is positioned underneath the heart. Thence, control of elevation, tilt and lateral position may all be obtained with the manipulator 10 in a single position.

The chambers 14a, 14b may be inflated with a gas, such as air, or with a sterile solution 13. Moreover, the gas or sterile solution may be heated or chilled to control the temperature of the heart. Chilling the heart, especially with a liquid, may be particularly advantageous during the procedure, for slowing it. It may also be advantageous to provide a warmed fluid, such as a fluid at approximately the body temperature or other desired temperature which is above the ambient fluid temperature.

Inflation and deflation may be accomplished by employing a reversible pump for pumping fluid into and out of the chambers 14a, 14b. Each of the chambers 14a, 14b preferably has an associated reversible pump 32a, 32b. However, other inflation means may be employed as well without departing from the principles of the invention as will readily be appreciated by those of ordinary skill. Such means include, for example, large volume syringes.

It is to be recognized that, while a specific cardiac manipulator for minimally invasive surgical procedures has been shown as preferred, other configurations could be utilized, in addition to configurations already mentioned, without departing from the principles of the invention. Particularly, the cardiac manipulator may be employed in surgical procedures requiring manipulation of other organs or tissues as well.

The terms and expressions which have been employed in the foregoing specification are used therein as terms of description and not of limitation, and there is no intention of the use of such terms and expressions of excluding equivalents of the features shown and described or portions thereof, it being recognized that the scope of the invention is defined and limited only by the claims which follow.

I claim:

1. An apparatus for manipulating body tissue in situ through an access aperture in a patient, the apparatus comprising:

a sac having a substantially flat, uninflated, low profile state, and an inflated state, and being sufficiently flexible in said substantially uninflated state to be configured with minimal selected dimensions for insertion through the access aperture and thereafter reconfigured in a substantially uninflated open configuration for placement proximate the body tissue which it is desired to manipulate, said sac defining a plurality of inflatable chambers, said chambers being in fluid communication with respective controllable sources of inflation for selectively changing the fluid volume of said chambers independently of one another, at least two of said chambers being disposed laterally adjacent one another so that, where said sac is placed proximate the tissue in the body of the patient, changing the fluid volume of one said chambers relative to the other said chambers tends to change the angular position of said tissue.

2. The apparatus of claim 1, wherein at least one of said chambers are formed out of said flexible sac.

3. The apparatus of claim 1, wherein at least one of said chambers are in fluid communication with a controllable source of deflation.

4. The apparatus of claim 3, wherein at least one of said chambers are connected by respective flexible fluid conduits for extending through the access aperture in the patient to a fluid pump to inflate and deflate at least one of said chambers.

5. The apparatus of claim 4, further comprising a stopcock disposed along at least one of said conduits for stopping fluid flow therethrough.

6. The apparatus of claim 1, wherein said sac is formed of two sheets of plastic bonded to one another.

7. The apparatus of claim 6, wherein said sac includes a periphery, a portion of which has an inwardly protruding edge.

8. A method for manipulating body tissue through an access aperture in a patient in a surgical procedure, the method comprising the steps of:

provided a sac having a substantially uninflated, low profile state, and an inflated state, and being sufficiently flexible in said substantially uninflated state to be configured with minimal selected dimensions for insertion through the access aperture and thereafter reconfigured in a substantially uninflated open configuration for placement proximate the body tissue which it is desired to manipulate, said sac defining a plurality of inflatable chambers, said chambers being in fluid communication with respective controllable sources of inflation for selectively changing the fluid volume of said chambers independently of one another;

manipulating said sac so that said sac assumes said minimal selected dimensions;

inserting said sac through said access aperture;

positioning said sac proximate the body tissue which it is desired to manipulate; and changing the fluid volume of one of said chambers relative to another of said chambers for controllable manipulation of the angular position, of the body tissue.

9. The method of claim 8, further comprising the steps of reconfiguring said sac into an open configuration.

10. The method of claim 8, further comprising the step of deflating at least one of said chambers to achieve said controllable manipulation.

11. The method of claim 8, wherein said step of inflating at least one of said chambers includes introducing a chilled fluid therein.

12. The method of claim 8, wherein said step of changing the fluid volume of one of said chambers relative to another of said chambers includes introducing a warmed fluid in said one of said chambers.

13. A method for manipulating the heart of a patient through an access aperture in the patient during minimally invasive cardiac surgery, comprising:

providing a sac having a substantially uninflated, low profile state and an inflated state, and being sufficiently flexible in said substantially uninflated state to be configured with minimal selected dimensions for insertion through the access aperture and thereafter reconfigured in an open configuration and a plurality of inflatable chambers disposed within said flexible sac, said chambers being in fluid communication with respective controllable sources of inflation;

manipulating said sac so that said sac assumes said minimal selected dimensions;

inserting said sac through said access aperture;

positioning said sac proximate the heart of the patient; and changing the fluid volume of one of said chambers relative to another of said chambers for controllable manipulation of the angular position of the heart.

14. The method of claim 13, wherein said flexible sac includes a first chamber and a second chamber, and wherein said step of positioning includes placing said first chamber underneath the bodily organ or tissue and placing said second chamber laterally against said bodily organ or tissue.

* * * * *